US009468718B2

(12) United States Patent  
Hung et al.

(10) Patent No.: US 9,468,718 B2  
(45) Date of Patent: Oct. 18, 2016

(54) MEANS AND METHOD FOR DETECTING FREE FLOW IN AN INFUSION LINE

(71) Applicants: David Tseng Ho Hung, Palo Alto, CA (US); David Pih, Milpitas, CA (US); Purushottam Amarnath Patil, San Diego, CA (US); John Michael Wyatt, San Diego, CA (US); Vincent James DeFrank, Temecula, CA (US)

(72) Inventors: David Tseng Ho Hung, Palo Alto, CA (US); David Pih, Milpitas, CA (US); Purushottam Amarnath Patil, San Diego, CA (US); John Michael Wyatt, San Diego, CA (US); Vincent James DeFrank, Temecula, CA (US)

(73) Assignee: Hospira, Inc., Lake Forest, IL (US)

( * ) Notice: Subject to any disclaimer, the term of this patent is extended or adjusted under 35 U.S.C. 154(b) by 155 days.

(21) Appl. No.: 14/019,745

(22) Filed: Sep. 6, 2013

(65) Prior Publication Data  
US 2014/0074030 A1   Mar. 13, 2014

Related U.S. Application Data

(60) Provisional application No. 61/698,636, filed on Sep. 8, 2012.

(51) Int. Cl.  
*A61M 1/00* (2006.01)  
*A61M 5/168* (2006.01)

(52) U.S. Cl.  
CPC ...... *A61M 5/16831* (2013.01); *A61M 2205/18* (2013.01); *A61M 2205/332* (2013.01); *A61M 2205/3365* (2013.01)

(58) Field of Classification Search  
CPC .................................................. A61M 5/16831  
USPC ............................................. 604/152; 702/47  
See application file for complete search history.

(56) References Cited

U.S. PATENT DOCUMENTS

| 4,972,842 | A  | * | 11/1990 | Korten et al. ................ 600/529 |
| 7,104,763 | B2 |   | 9/2006 | Bouton et al. |
| 7,258,534 | B2 | * | 8/2007 | Fathallah et al. .......... 417/477.2 |
| 7,360,999 | B2 |   | 4/2008 | Nelson et al. |
| 7,905,710 | B2 |   | 3/2011 | Wang et al. |
| 8,313,308 | B2 |   | 11/2012 | Lawless et al. |
| 2007/0062250 | A1 | * | 3/2007 | Krulevitch et al. ........... 73/1.16 |
| 2011/0172918 | A1 | * | 7/2011 | Tome ................... G01C 21/165 701/500 |
| 2013/0261993 | A1 |   | 10/2013 | Ruchti et al. |

\* cited by examiner

*Primary Examiner* — Edelmira Bosques  
*Assistant Examiner* — Leah Swanson  
(74) *Attorney, Agent, or Firm* — Michael R. Crabb

(57) ABSTRACT

A pump system and method of detecting/alerting for a possible unintended free flow condition in an administration set includes the steps of a) sampling force signals from a force sensor of the pump at a predetermined frequency; b) storing each of the sampled forces signal in a N-point circular buffer, where N is an integer greater than two; c) calculating a derivative dF/dt based on the two most recent samples; d) repeating step c) and when the most recently calculated derivative dF/dt exceeds a first predetermined threshold, then calculating a N-point moving average of the derivatives dF/dt; and f) when the N-point moving average exceeds a second predetermined threshold, generating a user perceptible alarm to alert the user that a flow stop open condition may have occurred.

3 Claims, 9 Drawing Sheets

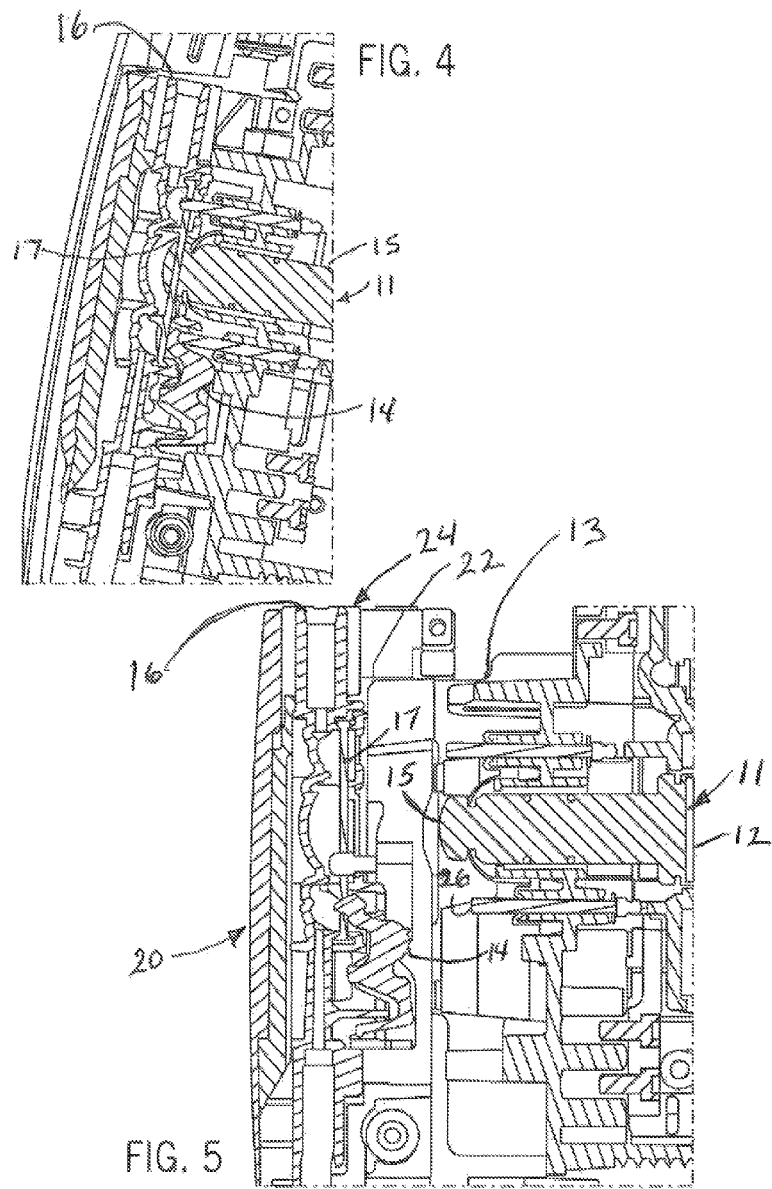

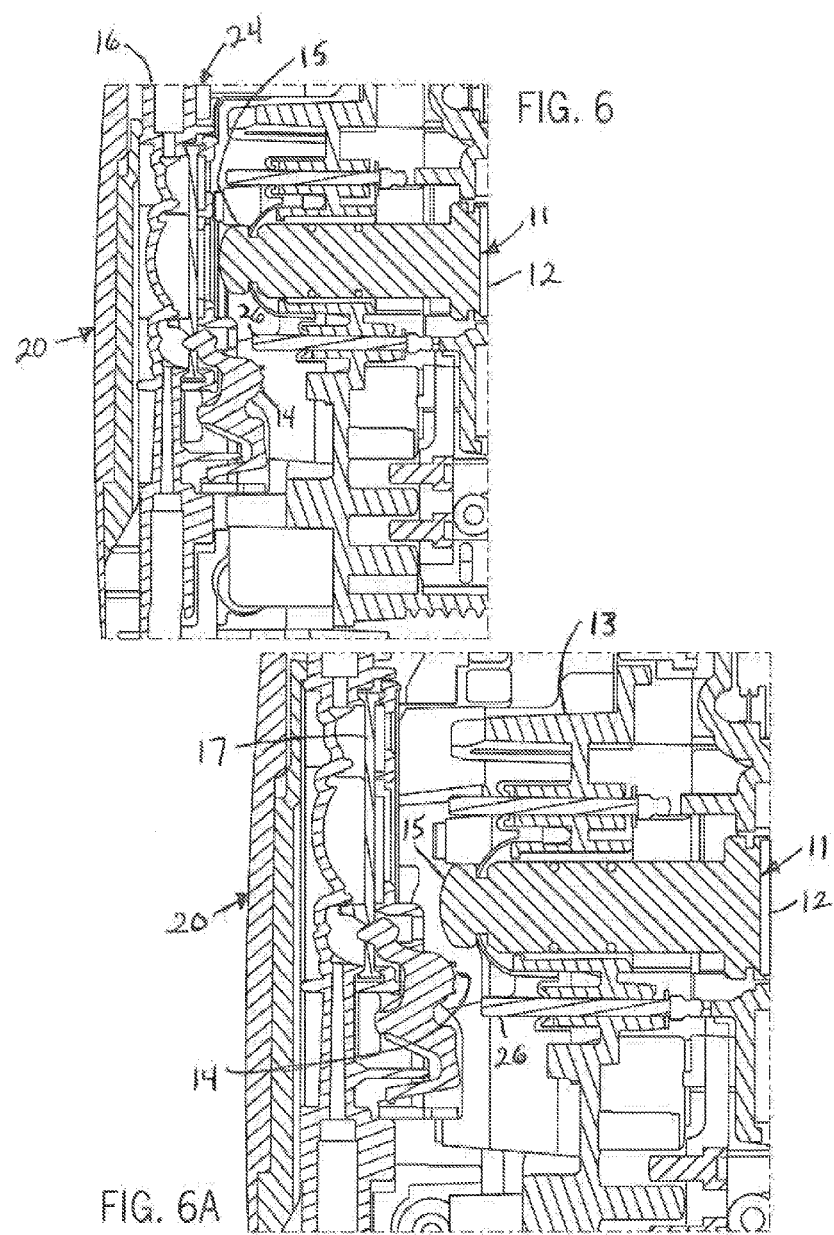

MEANS AND METHOD FOR DETECTING FREE FLOW IN AN INFUSION LINE

FIELD OF THE INVENTION

The present invention relates to the field of medication delivery devices and, more particularly, to electronic medication delivery devices and a method of detecting an unintentional free flow condition in an infusion line. By way of example and not limitation, the infusion line may be associated with an electronic medication delivery device such as an infusion pump.

BACKGROUND OF THE INVENTION

Electronic medication delivery devices such as infusion pumps are an invaluable tool in modern medical treatment. Many infusion pumps, such as the SYMBIQ™ infusion system sold by Hospira, Inc. of Lake Forest, Ill., can be programmed to deliver medications or other medical fluids to patients. The caregiver is then free to perform other tasks related to patient care, recordkeeping, etc. while the medical fluid is being delivered to the patient by the infusion pump 10 through an administration set 16 or infusion line.

In the case of the SYMBIQ™ infusion system the administration set includes tubing and a cassette with an inlet, and outlet and a pumping chamber covered by a flexible membrane 17 located between the inlet and outlet. A pumping mechanism 11 mounted on a pump chassis 13 repeatedly drives or forces a pumping element (a plunger) 15 that is normally in contact with the flexible membrane 17 forward into the membrane covering the pumping chamber and then retracts the plunger in a reciprocating motion. During retraction of the plunger, a passive inlet valve upstream of the pumping chamber opens, which allows fluid to be drawn into the pumping chamber as the plunger retracts. A passive outlet valve downstream of the pumping chamber closes to keep the fluid in the pumping chamber. As the plunger advances, pushing on the membrane covering the pumping chamber, the inlet valve is closed and fluid pressure builds in the pumping chamber until the plunger reaches its full extension or the fluid pressure reaches a predetermined level or cracking pressure. Then the outlet valve opens to allow the fluid to be displaced through the infusion line to the patient. Thus, medical fluids are displaced through the cassette of the infusion pump in a series of pulsing delivery cycles. The rate of fluid delivery can be controlled by a processor that controls the speed of a motor, such as a stepper motor, that moves the plunger. The processor that controls the pumping mechanism 11 is sometimes referred to as the pump mechanism control or PMC 18.

Administration sets usually have a slide clamp located somewhere on the tubing of the set. The slide clamp can be used as one means to close or open the infusion line, often whether the administration set is installed in the pump or not. In the case of administration sets for cassette type pumps like the SYMBIQ™ infusion system, the cassette also includes a selectively pivotable flow stop 14 that is normally closed but is pivoted opened by a distal pressure sensing pin 26 in the pump when the cassette is properly loaded in the pump. Generally the flow stop 14 is arranged to close automatically when the cassette is removed from the pump. The caregiver can also pivot the flow stop manually and open it to allow flow through the infusion line to prime the line, remove air bubbles and the like. Thus, the clamp and the flow stop normally provide two redundant means for preventing free flow in an administration set or infusion line. However, caregivers may forget to close the line with the clamp or need to unclamp the line at various times during installation and removal of the administration set from the pump. During those times, the flow stop is an important means for preventing unintended free flow of fluid through the administration set. Free flow is undesirable because it can result in spillage or waste of expensive or toxic medications when the administration set is not connected to the patient. Unintended free flow can also result in delivery of medication in a volume, rate or duration in excess of that prescribed when the administration set is connected to the patient.

The SYMBIQ™ pump has a motorized automatic cassette loader 20 with a movable carriage 22 that has an opening 24 formed thereon to receive a cassette of the administration set inserted by the user and moves the inserted cassette inwardly toward a fixed seat on the pump. See U.S. Pat. No. 7,258,534, which is incorporated by reference in its entirety herein, for further understanding of the automatic cassette loader assembly. When the caregiver wants to eject the cassette from the pump, the cassette loader automatically moves the carriage and the cassette away from the fixed seat. In the absence of external forces, the flow stop is designed to automatically pivot to its normally closed position. However, it has been discovered that if the caregiver pulls the administration set out of the cassette loader before the cassette loader reaches its fully opened position, the pivotable flow stop may strike the plunger, distal pressure pin, or other parts of the pump and be unintentionally forced opened so as to cause unintended free flow. More specifically, when a cassette is prematurely removed by the user while the cassette loader is opening, the cassette may bump the plunger, the distal pressure pin, or another structure on the pump. The flow stop may pivot and open if the flow stop surface collides with the distal pressure pin or the plunger with sufficient force.

While various things have been considered to address the above-mentioned problems, there is a need for an electronic medication delivery system and method that is able to simply, quickly and accurately detect an unintended or abnormal free flow condition and promptly alert the caregiver of the condition.

Thus, one objective of the present invention is to provide an electronic medication delivery device, such an infusion pump, equipped with a sensing device and method that will automatically detect an unintended or abnormal free flow condition and alert the caregiver of the condition.

These and other objectives, features, aspects and advantages of the invention will be apparent from the drawings, description and claims that follow.

SUMMARY OF THE INVENTION

The invention relates to a system and method of detecting an unintended, unexpected or abnormal free flow condition in an infusion line or administration set associated with an electronic medication delivery or medication delivery monitoring device such as an infusion pump. The system includes a processor, a memory containing program code executed by the processor and a force sensor associated with a pumping element or plunger of the pumping/monitoring mechanism. According to the method of the invention, the processor receives and processes force signals from the force sensor over time according to an algorithm defined in the program code stored in memory. The algorithm or method evaluates the force sensor signals and looks for a momentary force increase or "bump" in the signals that may indicate an unexpected, abnormal or unintended flow condition such as free flow is occurring.

In the example of an infusion pump that has a pumping mechanism with a plunger operating on a flexible diaphragm of a cassette equipped with a pivotable flow stop, and a force sensor on the plunger that sends force signals to the processor. A momentary force increase is captured as a bump signature on the plunger force versus time curve or profile. The bump detection algorithm in the pump mechanism control (PMC) software presumes a correlation in the bump signal with a possible flow stop opening, and triggers a user perceptible Check Flow Stop Alarm that can be audible, vibratory, or visually displayed on a user interface screen of the pump.

BRIEF DESCRIPTION OF THE DRAWINGS

FIG. 4 is a side sectional view of the pump mechanism of the pump of FIG. 1 with the cassette loaded into the pump mechanism.

FIG. 5 is a side sectional view of the pump mechanism of the pump of FIG. 1 wherein the carriage of the loader, which carries the cassette, is in a fully opened position so as to provide a space, clearance or gap between the flow stop of the cassette and the plunger and other structures of the pump mechanism.

FIG. 6 is a side sectional view of a pump mechanism, cassette and cassette loader, which illustrates that with some cassette designs the flow stop might collide with the distal pin if the cassette is pulled out prematurely, i.e., before the carriage of the loader is in a fully open position.

FIG. 6A is a side sectional view of a pump mechanism, cassette and cassette loader, which illustrates that the flow stop might collide with the plunger if the cassette is pulled out prematurely, i.e., before the carriage of the loader is in a fully open position.

DETAILED DESCRIPTION OF THE INVENTION

Figure 1:
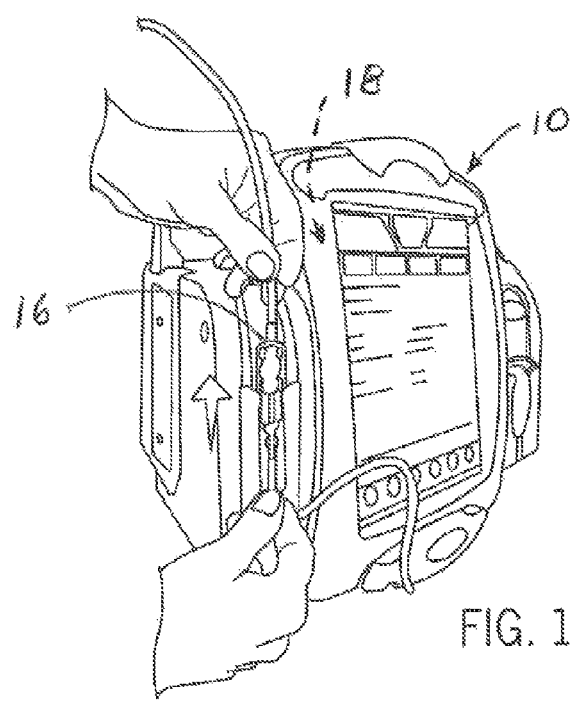
FIG. 1 is a perspective view of an infusion pump with an administration set that includes a cassette being removed from a carriage in an opened position of an automatic loader on the pump.
Figure 2:
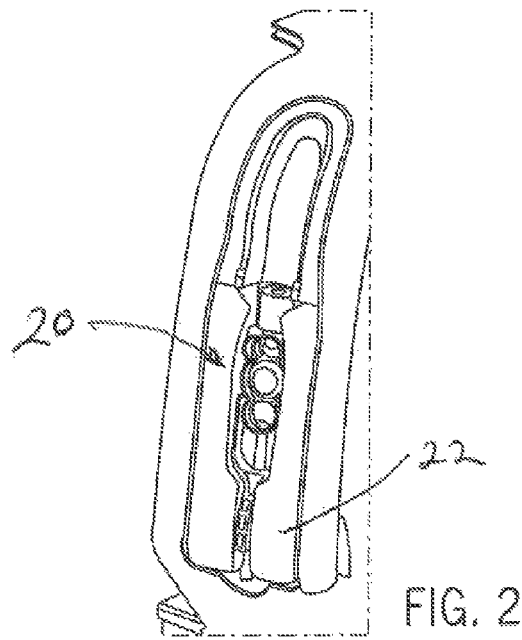
FIG. 2 is a partial perspective view of a loaded pump mechanism of the pump from FIG. 1 and shows a cassette of an administration set (with tubing omitted) installed in the carriage of the loader and in a closed position of the loader of the pump.
Figure 2A:
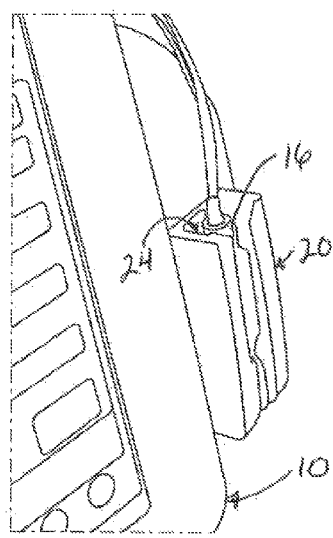
FIG. 2A is a partial perspective view of the infusion pump of FIG. 1 and shows the carriage of the loader in a fully open position with the cassette of the administration set supported inside.
Figure 3:
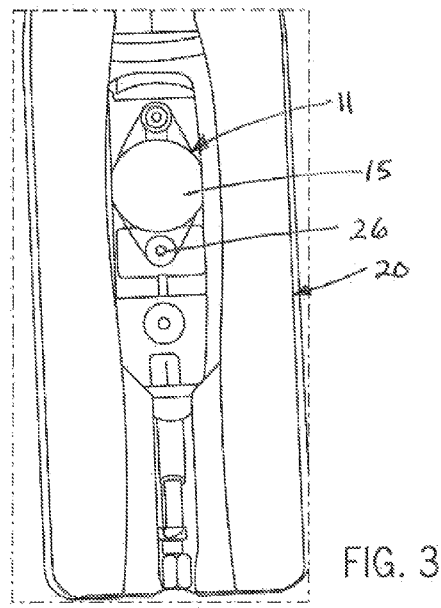
FIG. 3 is a front view of the pump mechanism of the pump of FIG. 1 and shows the proximal pin, distal pin, and plunger of the pump.
Figure 7:
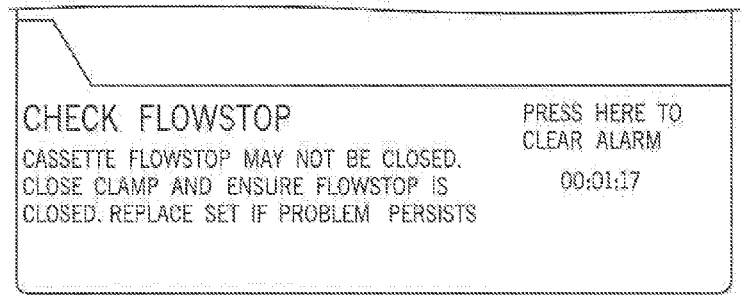
FIG. 7 is a partial screen display of the user interface of the pump of FIG. 1, wherein a Check Flow Stop alarm, warning or alert is generated and displayed along with instructions.

In the following detailed description, reference is made to the accompanying figures, which form a part hereof. In the figures, similar symbols typically identify similar components, unless context dictates otherwise. Illustrative embodiments described in the detailed description, figures, and claims are not meant to be limiting. Other embodiments may be utilized, and other changes may be made, without departing from the scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and made part of this disclosure.

A first bump detection algorithm attempted to allow the pump 10 to detect a plunger force sensor 12 condition where the flow stop 14 could be inadvertently opened during the cassette or administration set 16 removal process. This unrestricted (free) flow detection system uses the plunger force sensor as an indirect detector rather than increasing the cost of each administration set 16 by placing a direct flow sensor in the fluid flow path of the administration set or coupling an additional sensor to the administration set. The pump mechanism controller or PMC processor 18 via software embedded in its memory calculated a force that indicates that the cassette loader assembly 20 or door is closed. The "Door Closed" force is calculated as the average force value for the time period starting 1 second after completion of depressurization and continuing for up to 2 seconds until a delivery starts. While the door is opening, if the plunger force exceeds the "Door Closed" force, the "Pumping Plunger Peak" force condition is met; see illustration in FIG. 8. The plunger force derivative as the difference between the current reading and the previous reading is calculated. If the derivative exceeds 23000 decigram force/seconds for two consecutive times, then the derivative condition is met. When both conditions are met, then Check Flow Stop Alarm is triggered.

A collision or bump by the flow stop on the cassette with the plunger or any other structure on the pump generates a collision signal. The embedded software of the system makes a real-time decision to trigger a flow stop alarm or not based on the profile of the collision signal. The new detection algorithm as mentioned herein significantly improves the pump's ability to detect the collision accurately and sensitively enough so that a small signal barely above the noise levels can be detected.

Figure 8:
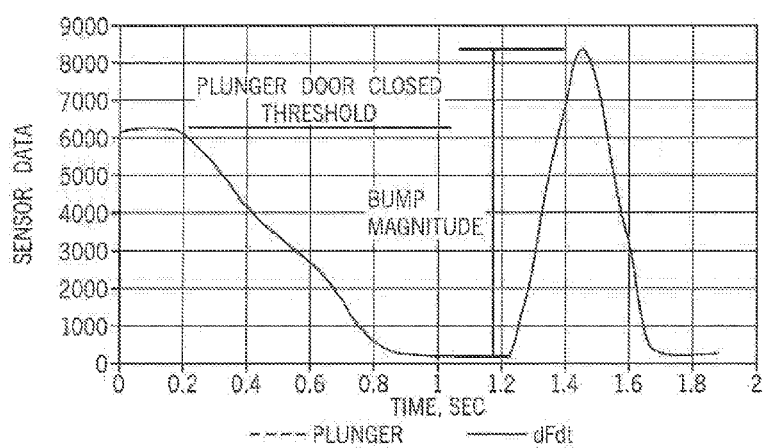
FIG. 8 is a graph of plunger sensor force versus time during opening of the carriage or loader door, which illustrates first method of detecting a bump or collision of the flow stop with the plunger.
Figure 9:
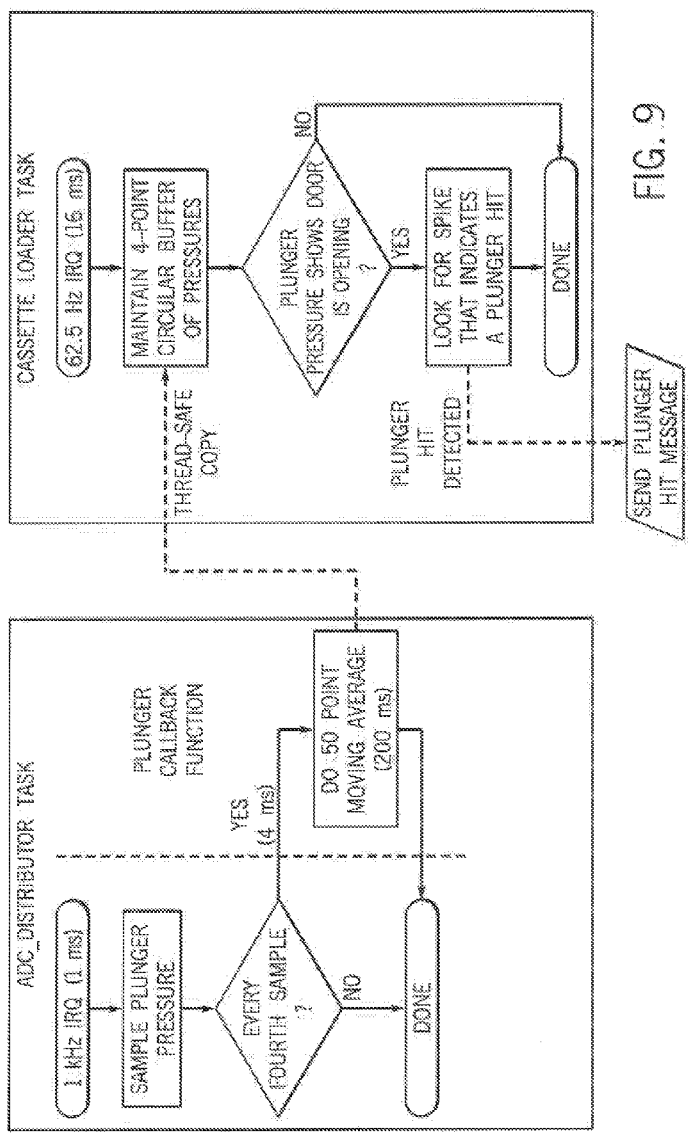
FIG. 9 is a flow chart that illustrates a high level view of activities during the opening of the loader in a second method of detecting a bump or collision of the flow stop with the plunger according to the present invention.
Figure 10:
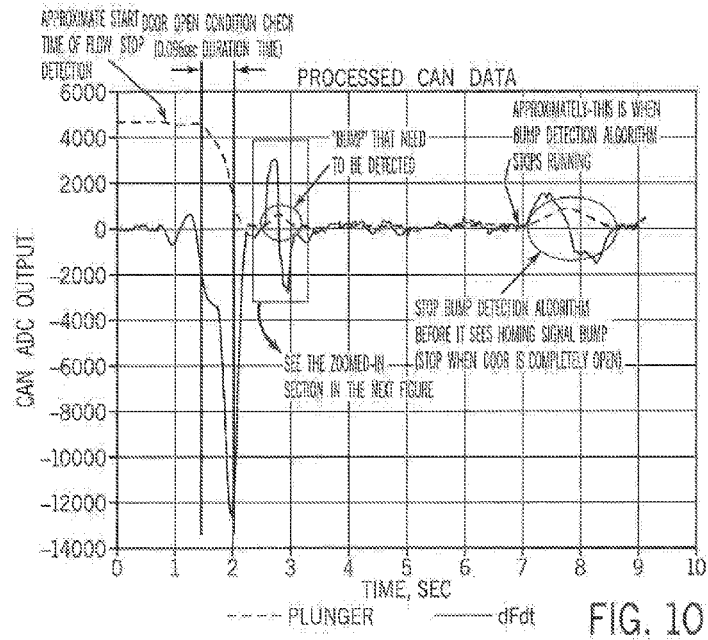
FIG. 10 is a graph showing plunger force sensor CAN data processed according to the second bump detection method and includes plunger force and dF/dt with CAN ADC values (in decigrams) on the Y axis and time (in seconds) on the X axis
Figure 11:
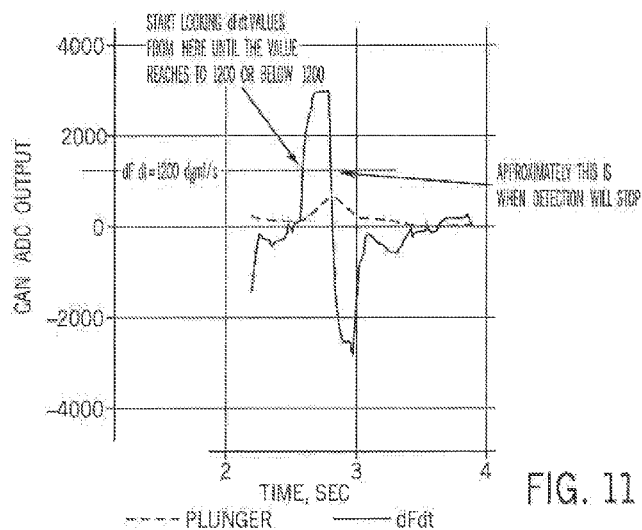
FIG. 11 is an enlarged portion of the graph of FIG. 10 taken from the area designated 11-11 and shows greater detail regarding bump detection in the second method.
Figure 12:
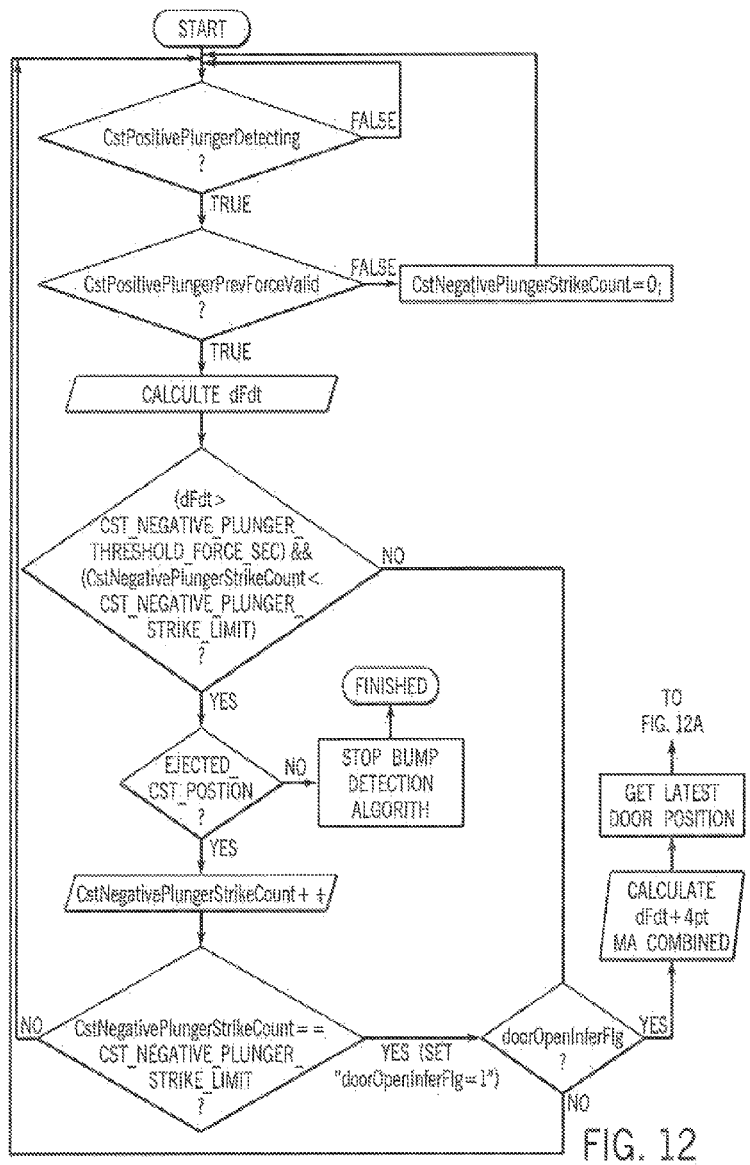
FIG. 12 is a flow chart that illustrates the bump detection according to the second method.
Figure 12A:
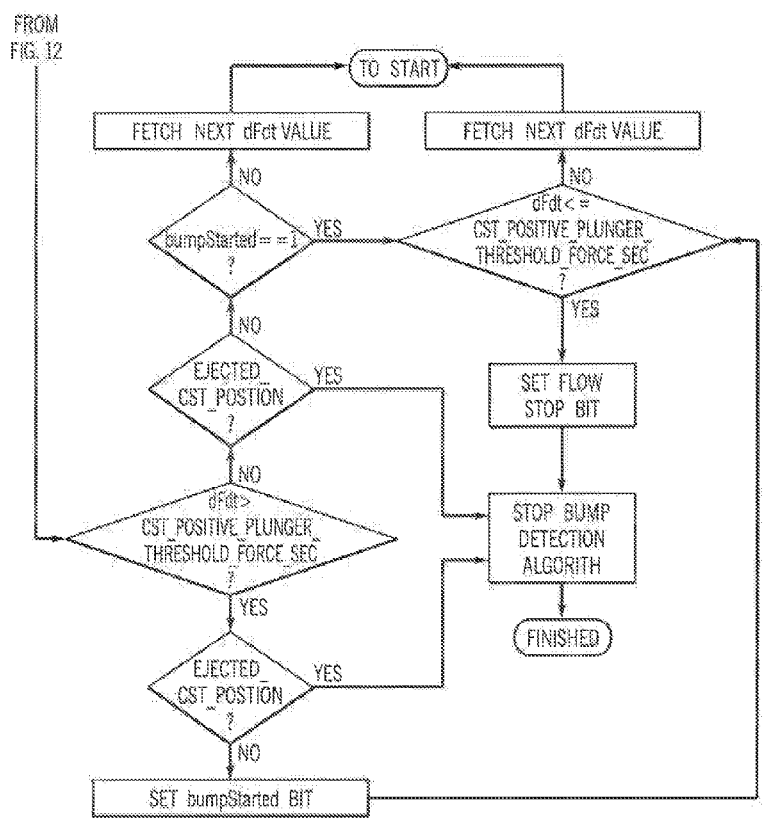
FIG. 12A is a continuation of the flow chart of FIG. 12 and further illustrates the bump detection according to the second method.

Investigation teams performed tests on fifteen dual-channel pumps and collected 240 test cases during which unrestricted flow events occurred without the Check Flow Stop Alarm being triggered under the first bump detection algorithm described herein and illustrated in FIG. 8. This led to several conclusions, observations and recommendations. In the first bump detection algorithm, the plunger force value must exceed the plunger door-closed baseline or threshold condition. This condition effectively prevented small bumps below the threshold from being detected. Thus, this condition should be eliminated to detect very small bumps. The force derivative condition was not met, especially for the small bump signals. The derivative threshold at 23,000 decigram/seconds was set too high. A new threshold is needed to make the bump detection algorithm more robust.
Second Plunger Bump Detection Algorithm or Method A second, new and improved bump detection algorithm makes some changes in the PMC software. For the reasons mentioned above, the "Door-closed" force condition is eliminated. A four-point moving average force derivative threshold is used and set to 1,800 decigram/seconds. This enables the PMC software to detect very small bumps while reducing the false positive or nuisance alarms that could occur due to plunger noise signals. There may be a possibility that the flow stop valve could open if 1,800 decigram/second threshold is NOT crossed since the plunger force sensor detects bumps, but not the actual position of flow stop.

Table 1 shows the comparison between the first and second bump detection algorithms.

TABLE 1

| Version Name | SECOND | FIRST |
|---|---|---|
| SW Name | (4-pt dF/dt Moving Average) | (dF/dt only) |
| Raw Data Sampling, Hz | 250 | 250 |
| 50-pt Moving Average | Yes | Yes |
| Down-sample 4:1 | Yes | Yes |
| dF/dt Rate, Hz | 62.5 | 62.5 |
| dF/dt Implementation | [F(0) − F(−4)]*62.5/4 | [F(0) − F(−1)]*62.5 |
| dF/dt Threshold | 1,800 | 23,000 |
| Strike Counter for dF/dt | Eliminated | 2 consecutive times |
| Plunger Door-closed Threshold | Eliminated | Must exceed |

Note that the above difference equation, $[F(0)-F(-4)]*62.5/4$, was a simplified version of two other equivalent implementations in the software:
1. Taking four plunger data point moving averages and then take derivative on the moving averages; or
2. Taking derivatives on four plunger data points and then taking moving averages on the derivatives.
Also note that the new second bump detection algorithm treats any tiny bump as noise if the bump exists and falls below the 1,800 decigram/sec dF/dt threshold.
Threshold Selection The final 1,800 decigram/seconds decision threshold was iteratively chosen by analyzing test data of the SYMBIQ™ pump plunger bump signals by balancing miss-detection (i.e. unrestricted flow events without the flow-stop alarms) and over-sensitive level (i.e. that can cause nuisance alarms due to the noise levels of the plunger force sensor signals).
Four-Pt Moving Average Selection Moving average can be viewed as an example of a low-pass filter used in signal processing to attenuates (reduces the amplitude of) noise components of the signal. The noise can come from high-frequency component from the sensor itself or thermal noise. The noise level can be significant when signal level is low. With the filtering technique (i.e. moving average), the algorithm is able to distinguish the useful component of signals from noise components of the signal.

The four-pt moving average was selected and optimized based on the plunger bump signal's bump duration characteristics (i.e. the rising time of the smallest plunger bump signal) and iterative testing for optimal detection performance and least amount of memory requirement. However one can appreciate that any N-point circular buffer and N-point moving average would yield improvement over the first method if N is a positive integer greater than two.
Memory Requirement Related to Four-Pt Moving Average Selection The rising time span of the smallest bump is close to four times the sampling time of the data processing after 4:1 down-sampling. The embedded software needs to hold F(0), F(1), F(2), F(3), and F(4) in memory for $[F(0)-F(-4)]*62.5/4$ implementation. There were two memory spaces in the previous detection algorithm. This is an increase in cost of only three memory spaces in return for the optimum noise suppression and event detection performance.
Verification Results Software was implemented and loaded onto SYMBIQ™ pumps for verification testing. The verification test was aided by the verification test fixture and test system. 1101 test cases for the second method and 1091 test cases for the first method were collected. The 2192 cases were analyzed and the verification test is summarized below in Table 2.

TABLE 2

| Verification Software Version Number | SECOND | FIRST |
|---|---|---|
| Bump Detection Algorithm | Second | First |
| Verification Test Fixtures Used | Yes | Yes |
| Pump Mechanisms Required | 20 | 20 |
| Pump Mechanisms Completed | 20 | 20 |
| Total Test Cases Completed | 1101 | 1091 |
| Cases of Correct Decision Making | 1101 | 373 |
| Premature Cassette Pulls | 742 | 731 |
| Flow Stop Alarms Triggered | 741 | 11 |
| Flow Stop Valve Open or Unrestricted Flow Events | 103 | 119 |
| Alarms for the Unrestricted Flow Events | 103 | 9 |
| Nuisance Alarm (False Positive; No Bump Occurred) | 0 | 0 |
| Miss Detection (False Negative; Bump Occurred) | 0 | 718 |
| Improvement Ratio | 718/0 = ∞ | |

Limitation on Unrestricted Flow Applications

During verification testing using the second method, there were 638 (=741−103) test cases in which flow stop alarm events occurred without no unrestricted flow events because of the correct bump detection. The 638 cases could be treated as nuisance alarms. The bump detection algorithm uses plunger force signal as a proxy for detecting whether the flow stop is open or not. It is not a 100% reliable for detecting unrestricted flow; in fact it is only 103/741=14% correct in detecting unrestricted flow. This plunger force sensor use has its limitations. The algorithm is erring on the side of the caution rather than negligence. Nevertheless, the bump detection algorithm does what is supposed to do.
Embedded Software Implementation In the embedded software, the Cassette Loader Task maintains the status of the cassette door position and handles all commands to open and close the door. When the door is commanded to open, the Plunger Hit Algorithm variables are reset and a 16 ms continuous timer is started for the purpose of monitoring the plunger pressure. The pressure derivative is calculated and once the pressure shows a sudden drop, which is consistent with the door physically starting to open, all subsequent pressure samples will be presented to the Plunger Hit Algorithm for processing. Once the door has completed opening, the 16 ms timer is stopped. This ensures that the algorithm will not falsely alarm when the plunger starts to move to the Home position (which starts once the door is fully open). Special care has been taken while implementing the algorithm, as listed below, 1) Real-time, in that one process starts the door movement (Air Motor PRD timer after air sensor is opened) but a different process stops it (LPA Monitor when it detects that door is open).
2) Real-time, in that it cannot store data and process it afterwards, so must use the minimum amount of historical pressure data.
3) Real-time, in that the door is moving while the algorithm is running, so the algorithm must consume as little time as possible.
4) Memory optimized, in that minimum number of variables used to use minimum software stack
5) Real-time, in that taking an efficient decision when to start flow stop algorithm and when to stop, while door is moving.
6) Real-time and memory optimized, in that care has been taken not to overload a processor
7) Real-time, in that care has been taken that every sample is being processed, so that no dropping of samples occur
8) Care has been taken with the loop optimization, avoiding dead code introduction, local and global variable placement.
9) Real-time, in that Detection and report the medical event immediately when it occurs.

The 16 ms Timer interrupt handler processes plunger pressure samples in real time. The logic for each sample is as follows:

```
Store current sample in a 4-point circular buffer
Calculate Derivative of the two most recent samples
IF Derivative exceeds Door Opening Threshold THEN
    Set doorOpenInferFlag = 1
END IF
IF doorOpenInferFlag == 1 THEN
    Calculate Force Derivative over a 4-point average.
    IF Force Derivative Exceeds the defined threshold THEN
        BumpStarted = 1          // Leading edge of the bump
    END IF
    IF Force Derivative is Below the defined threshold THEN
        IF BumpStarted == 1 THEN
            Send Plunger Hit Message      // Trailing edge of the bump
            Stop 16 ms Timer
        END IF
    END IF
END IF
```

In conclusion, the second plunger force sensor bump detection algorithm has the following advantages:

1. Significantly reduce miss detection rate for unrestricted flow that may affect patient safety
2. Able to catch very tiny bumps whose force profile rises barely above the baseline signal levels
    a. Robust or insensitive to noise floor or plunger signal baseline time spans; no calibration is needed
    b. The variation of plunger baseline from pump to pump is eliminated since derivative of the constant (baseline level) is zero or close to zero. This makes the baseline variations in the system insensitive.
    c. Algorithm is robust over a wide dynamic range. If tiny bumps are caught, then any bump whose dF/dt is greater that minimum dF/dt can be caught.
3. Algorithm that uses four-point moving average dF/dt reduces noises in the dF/dt and is more robust than the single-point dF/dt technique.
4. No other signal processing/filtering required; filtering would involve latency and more memory space and thus incur cost.
5. The software implementation uses only few more memory space to achieve high-sensitivity in catching small bumps.
6. Applications could be or may be found in medical device event detections for activation, decision-making, safety, etc.
7. Applications could be or may be found in event detections such as touch screen, key pad and other user-interface design areas.
8. Applications could be or may be found in motion sensors, intelligent/reliable motion processing solutions, and motion-based user interface for consumer electronics such as console and portable video gaming devices.

What is claimed is:

1. An infusion pump, comprising:
    a pump chassis;
    a pump mechanism controller supported by the pump chassis and including a processor and a memory;
    a pump mechanism mounted on the pump chassis and including a plunger controlled by the pump mechanism controller;
    a loader assembly including a carriage movably mounted to the pump chassis, the carriage having an opening formed thereon for receiving an administration set removably installable in the opening by a user, the administration set including a flexible membrane covering a portion of the administration set and a normally closed pivotable flow stop adjacent to the membrane covered portion, the carriage of the loader assembly being movable from 1) a fully open position wherein the user can remove the administration set with clearance between the flow stop and the plunger, and 2) a fully closed position wherein the membrane is engaged by the plunger to pump fluid through the administration set and the plunger is free from contact with the flow stop;
    a plunger force sensor connected to the plunger for sending plunger force signals to the pump mechanism controller;
    the memory including program code stored therein, the program code being executed by the processor to:
        a) sample force signals from the plunger force sensor at a predetermined frequency;
        b) store each of the sampled force signals in a four point circular buffer;
        c) calculate a derivative dF/dt based on the two most recent samples;
        d) repeat step c) and when the most recently calculated derivative dF/dt exceeds a first predetermined threshold, then calculate a four point moving average of the derivatives dF/dt;
        e) when the four point moving average exceeds a second predetermined threshold, generate a user perceptible alarm to alert the user that a plunger hit/flow stop open condition may have occurred; and
    wherein the program code is executed by the processor while the carriage of the loader assembly is moving between the fully closed position and the fully open position.

2. The infusion pump of claim 1 wherein the user perceptible alarm is generated on a display screen on the pump.

3. A method of detecting and alerting for a possible unintended free flow condition in an administration set for intravenous medical fluids while the administration set is being removed from an infusion pump, the method comprising the steps of:
   a. sampling force signals from a force sensor of the pump at a predetermined frequency;
   b. storing each of the sampled force signals in a four point circular buffer;
   c. calculating a derivative dF/dt based on the two most recent samples;
   d. repeating step c) and when the most recently calculated derivative dF/dt exceeds a first predetermined threshold, then calculating a four point moving average of the derivatives dF/dt;
   e. when the four point moving average exceeds a second predetermined threshold, generating a user perceptible alarm to alert the user that a flow stop open condition may have occurred;
   wherein the steps start after an administration set receiving carriage of an automated loader assembly of the infusion pump begins to move away from a fully closed position and are completed before arrival of the carriage of the automated loader assembly at a fully open position.

\* \* \* \* \*